US010769580B2

(12) United States Patent
Sobie (10) Patent No.: US 10,769,580 B2
(45) Date of Patent: *Sep. 8, 2020

(54) METHOD AND APPARATUS FOR INVENTORY CONTROL IN MEDICAL TREATMENT AREAS

(71) Applicant: CareFusion 303, Inc., San Diego, CA (US)

(72) Inventor: Robert Andrew Sobie, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 660 days.

This patent is subject to a terminal disclaimer.

(21) Appl. No.: 14/673,774

(22) Filed: Mar. 30, 2015

(65) Prior Publication Data

US 2015/0205923 A1 Jul. 23, 2015

Related U.S. Application Data

(63) Continuation of application No. 12/327,623, filed on Dec. 3, 2008, now Pat. No. 8,996,393.

(51) Int. Cl.
| | | |
|---|---|---|
| *G16H 40/20* | (2018.01) | |
| *G16H 10/60* | (2018.01) | |
| *G06Q 50/22* | (2018.01) | |
| *G06Q 10/08* | (2012.01) | |
| *G06Q 50/24* | (2012.01) | |

(52) U.S. Cl.
CPC ......... *G06Q 10/087* (2013.01); *G06Q 50/22* (2013.01); *G06Q 50/24* (2013.01); *G16H 10/60* (2018.01); *G16H 40/20* (2018.01)

(58) Field of Classification Search
CPC ...... G06Q 50/22; G06Q 50/24; G06Q 10/087; G16H 10/60; G16H 40/20
USPC ............................................................ 705/3
See application file for complete search history.

(56) References Cited

U.S. PATENT DOCUMENTS

| | | | |
|---|---|---|---|
| 7,260,597 B1 * | 8/2007 | Hofrichter | .......... H04L 12/2803 707/999.01 |
| 7,639,136 B1 * | 12/2009 | Wass | ...................... G06Q 10/08 340/572.1 |
| 7,698,156 B2 * | 4/2010 | Martucci | ............. G06F 19/3412 705/2 |
| 2003/0009244 A1 | 1/2003 | Engleson et al. | |
| 2003/0025604 A1 * | 2/2003 | Freeman | .............. A61B 5/7475 340/573.1 |
| 2004/0019464 A1 | 1/2004 | Martucci et al. | |
| 2004/0030724 A1 * | 2/2004 | Rosenquist | .......... G06Q 10/087 |
| 2004/0078231 A1 | 4/2004 | Wilkes et al. | |
| 2004/0172302 A1 * | 9/2004 | Martucci | ............. A61B 5/0002 705/2 |

(Continued)

FOREIGN PATENT DOCUMENTS

WO WO-2006051464 A1 * 5/2006 ........... A61B 5/0205

*Primary Examiner* — Hiep V Nguyen
(74) *Attorney, Agent, or Firm* — Morgan, Lewis & Bockius LLP (57) ABSTRACT

Methods and systems for controlling inventory in a medical facility include providing a medical device into a medical treatment area within a wireless range of a medical facility network and automatically identifying the medical device upon introduction into the medical treatment area. Patient records are automatically updated to reflect that the medical device has been assigned to a patient.

17 Claims, 7 Drawing Sheets

(56) References Cited

U.S. PATENT DOCUMENTS

| | | |
|---|---|---|
| 2005/0102167 A1 | 5/2005 | Kapoor |
| 2005/0133027 A1 | 6/2005 | Elaz et al. |
| 2007/0016450 A1 | 1/2007 | Bhora et al. |
| 2007/0112602 A1 | 5/2007 | Bellon et al. |
| 2007/0129609 A1 | 6/2007 | Kawasaki |
| 2007/0135965 A1 | 6/2007 | Nguyen et al. |
| 2007/0272746 A1* | 11/2007 | Ortiz .................. G06K 17/00 235/385 |
| 2007/0273517 A1 | 11/2007 | Govind |
| 2007/0290030 A1* | 12/2007 | Fox .................. G06Q 10/087 235/375 |
| 2008/0221928 A1* | 9/2008 | Garcia ................ G06Q 50/24 705/3 |
| 2009/0231124 A1* | 9/2009 | Klabunde ........... A61B 5/0205 340/539.12 |

* cited by examiner

METHOD AND APPARATUS FOR INVENTORY CONTROL IN MEDICAL TREATMENT AREAS

RELATED APPLICATIONS

This application is a continuation of U.S. patent application Ser. No. 12/327,623, filed Dec. 3, 2008, entitled "Method and Apparatus for Inventor Control in Medical Treatment Areas," which is related to U.S. patent application Ser. No. 12/327,614, filed Dec. 3, 2008, entitled "Method and Apparatus for Automatically Integrating Into A Medical Facility Network," which are both incorporated herein by reference in their entirety.

FIELD

The present disclosure relates generally to a method and apparatus for inventory control in a medical treatment area in an institution, such as a medical facility.

BACKGROUND

Problems have long existed in maintaining an accurate accounting of tools, parts and components during complex procedures. For example, keeping accurate track of the medical devices and medications used during medical procedures has been one of the major concerns of healthcare facilities for many years. This problem is particularly costly in many ways for large sized hospitals comprising scores of operating rooms, and millions of dollars of medical device inventory. For example, errors in the dispensing, administration and prescribing of medications and medical treatments have resulted in an unacceptably large number of adverse reactions, including many deaths and permanent impairments, leading to higher insurance costs and expensive legal judgments.

Additionally, medical devices may be displaced during transfer from and to surgical processing departments, sterilization process and/or operating room procedures. Even if the medical device is brought into the medical treatment area, quite often the use of the medical device within the medical treatment area for the patient is not recorded. Consequently, these medical devices go unaccounted for in the billing process. Further, "renegade" medical devices, such as those brought into an operating room by a sales representative, may be implanted into a patient, with no such record of the device ever being in the medical facility. Worse yet, if there is a recall of the renegade medical device, it is virtually impossible to determine which patient received the device because of the gap in record keeping.

There are several computerized solutions available on the market, which provide a level of tracking of medical devices. Many systems use bar-code label scanning and/or magnetic stripe card technology to facilitate tracking of medical devices through the decontamination process; the inspection, assembly, and packaging process; and the sterilization cycle. For medical devices such as surgical instruments, these systems consider any particular set as a unit and provide a list of the instruments comprising the set.

While the cost of such bar-code labels and magnetic stripe cards is low, the amount of information that can be embedded or coded in either of these media is also relatively low, even where complex bar codes such as a 2-D bar code is employed. In addition, most bar code readers are read-only devices that can only read the information stored in the bar code and cannot store any additional information in the bar-code label.

Moreover, bar-code media require a "line-of-sight" communication path between device and reader, and magnetic stripe media require a direct or close contact communication path between device and reader at a suitable "swiping speed," and the reliability of correct reading is about 80-90%. Repeated passes of the device in front of the bar-code reader or swipes of the card reader create delay and annoyance and/or can produce record errors. Such problems are not overcome with more complex bar codes, and can actually be exacerbated where the bar code elements are smaller in size and thus more sensitive to smudging and dirt.

Absent a network connection to a computer, prior art tracking systems do little more than to read the information stored in the bar code or magnetic stripe, and cannot detect errors therein, which is a particular disadvantage in relation to medication and medical devices wherein errors in dispensing and/or using the medication or device can have serious, if not fatal, consequences. Furthermore, prior art tracking systems do not account for the introduction of renegade medical devices into the healthcare facilities.

SUMMARY

Accordingly, there is a need for apparatus and method that can assist in the dispensing and administration of medical devices and/or medical treatment. Desirably, such apparatus and method should facilitate tracking a medical device at various stations and associating the medical device with a desired recipient, i.e., a patient. It would further be advantageous for the apparatus and method to have a high correct-reading ability (e.g., near 100%) and be in communication with a central computer and online information system.

The presently disclosed embodiments are directed to address one or more of the above-stated needs, described above, as well as providing additional features that will become readily apparent by reference to the following detailed description when taken in conjunction with the accompanying drawings.

Certain disclosed embodiments are directed to a method of controlling inventory in a medical facility. The method comprises providing a medical device into a medical treatment area within a wireless range of a medical facility network and automatically identifying the medical device upon introduction into the medical treatment area. The method further comprises automatically updating a patient record to reflect that the medical device has been assigned to a patient.

Certain disclosed embodiments are directed to a system of controlling inventory in a medical facility. The system comprises a medical facility network and a medical device within a wireless range of the medical facility network. The medical facility network is configured to automatically identify the medical device upon introduction into a medical treatment area and retrieve a medical device record associated with the medical device.

Certain disclosed embodiments are directed to another method of controlling inventory in a medical facility. The method comprises providing a medical device into a medical treatment area within a wireless range of a medical facility network and automatically identifying the medical device upon introduction into the medical treatment area. The method further comprises automatically retrieving a medical device record associated with the medical device from the medical facility network and displaying the medical device record to a user.

The present invention is not limited to the aforementioned embodiments, and other features of the embodiments will become apparent after review of the hereinafter set forth Brief Description of the Drawings, Detailed Description, and the Claims, or may be learned by practice of the invention.

BRIEF DESCRIPTION OF THE DRAWINGS

The foregoing aspects of the embodiments described herein will become more readily apparent by reference to the following detailed description when taken in conjunction with the accompanying drawings wherein.

DETAILED DESCRIPTION

Reference will now be made in detail to the presently disclosed embodiments, examples of which are illustrated in the accompanying drawings, wherein like reference numerals refer to like elements throughout.

Prior art tracking systems typically do not track medical devices along their entire processing and use path. Additionally, prior art tracking systems do not have reliable, essentially 100% correct reader performance, without requiring human intervention, as is desirable for providing complete and accurate records. Embodiments of the present invention address such shortcomings by providing systems and methodologies for controlling inventory of medical devices.

Figure 1:
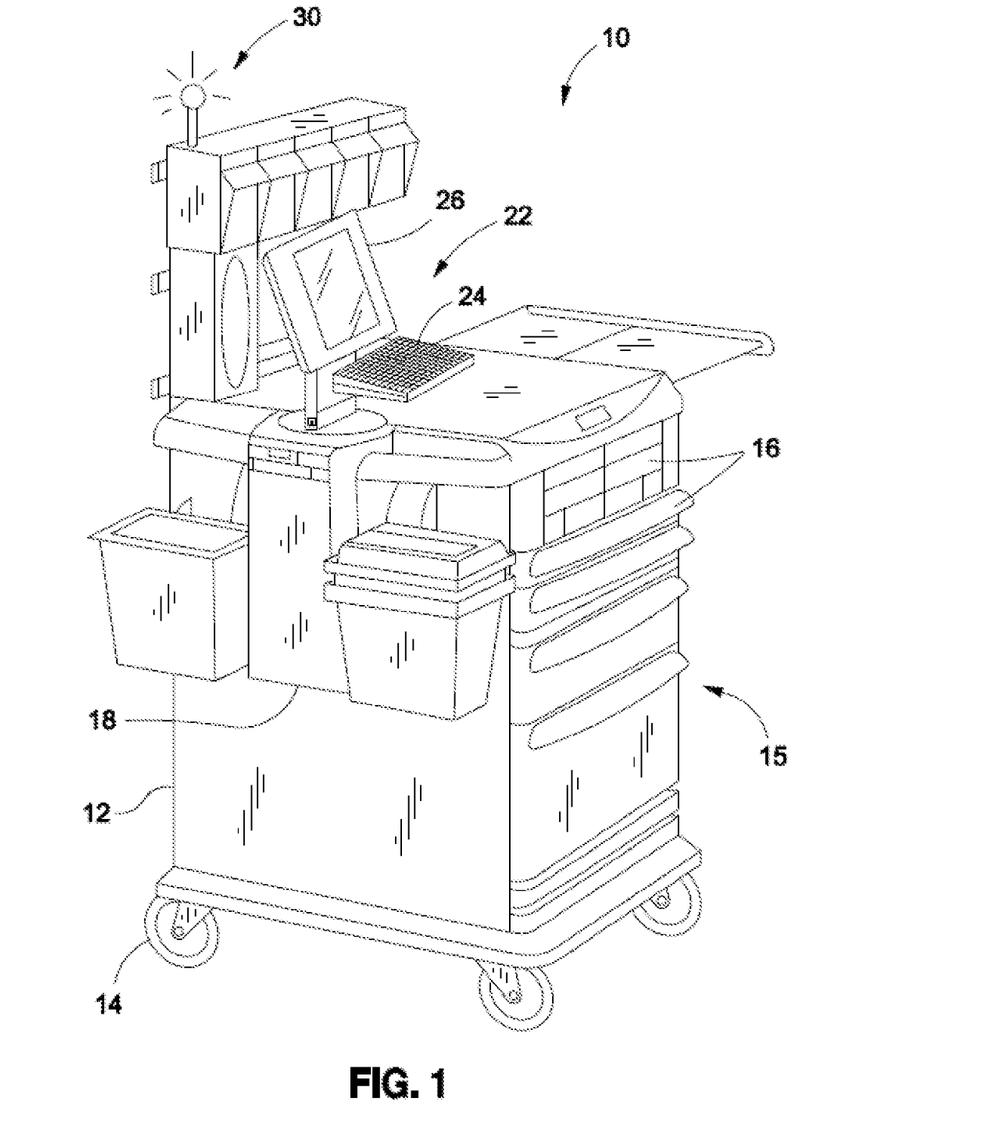
FIG. 1 is a perspective depiction of an exemplary medical device, according to disclosed embodiments.

Referring initially to FIG. 1, embodiments of the present invention may be employed with or as part of medical device 10, such as a mobile or stationary dispensing station 15 that is used in an institution to controllably dispense medication and other items for use in treating patients. Such an exemplary medical device is described in U.S. Patent Application Publication No. 20070135965, entitled "System and Method for Storing Items and Tracking Item Usage," incorporated by reference in its entirety. However, the dispensing station 15 is but one example of a medical device for purposes of this disclosure. The term "medical device" as used herein refers to any device capable of wireless communication, such as dispensing station 15 or a properly equipped prosthetic limb or an infusion pump, etc., that is configured for wireless communication.

As shown in FIG. 1, the dispensing station 15 comprises cabinet 12 supported by wheels 14 so that it may be moved easily to medical treatment areas throughout a medical facility, such as into an operating room. In the exemplary embodiment shown, the cabinet 12 holds sliding trays or drawers 16 of varying shapes and sizes for storing a wide variety of items. The number and configuration of the drawers 16 may be modified to meet the needs of the institution in which the dispensing station 15 is used.

Reference numeral 30 refers to a schematically depicted a wireless communication device that provides wireless communication capability to the medical device 10. The depiction is representational only, and is not meant to depict any actual physical configuration or location of any particular wireless communication device.

Figure 2:
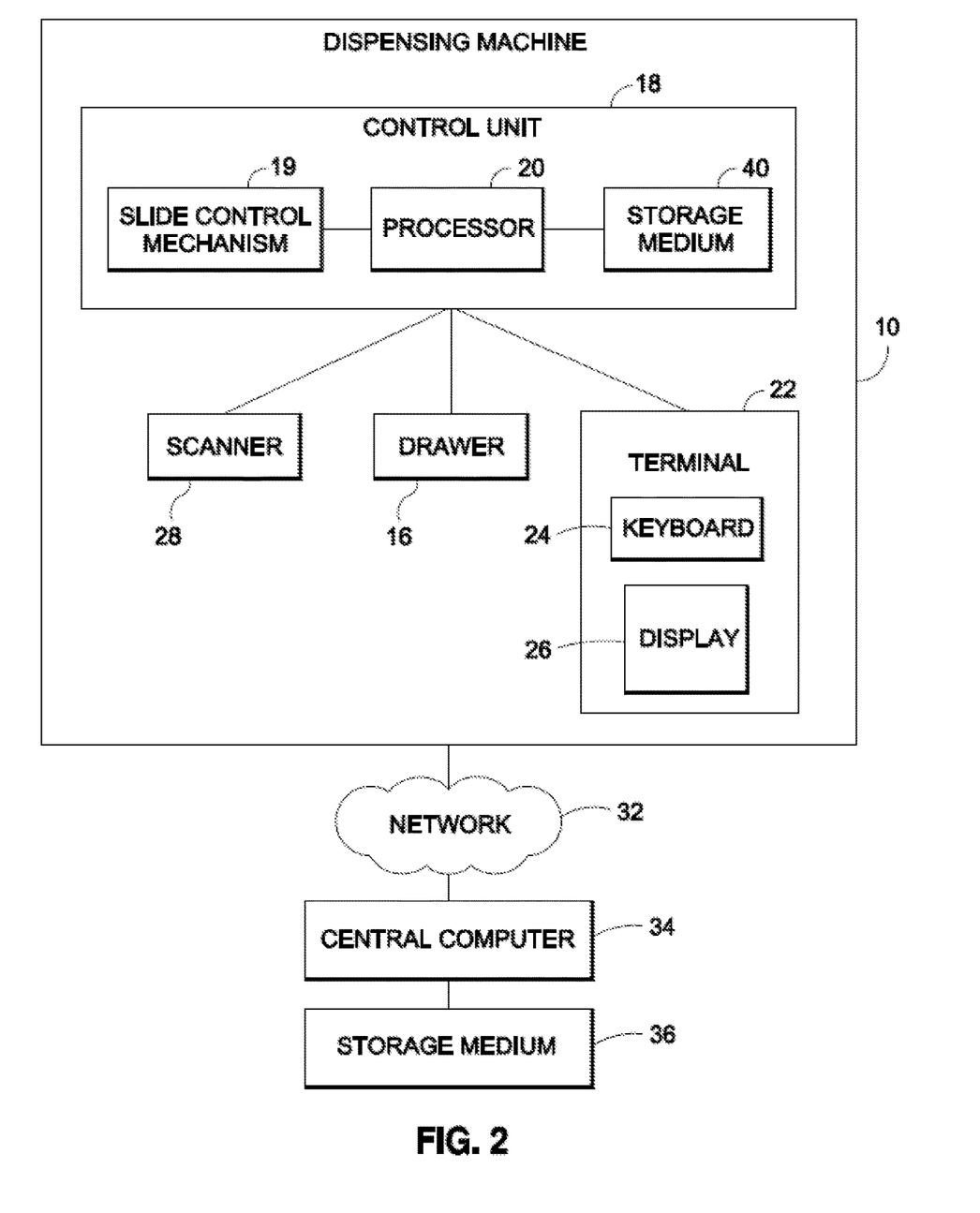
FIG. 2 is a block diagram of an exemplary operating system of the medical device of FIG. 1 and shows a network connection between the medical device, a central computer, and a storage medium, according to disclosed embodiments.

Referring now to FIG. 2, in some embodiments, drawers 16 are coupled to a control unit 18 for limiting and tracking user access to stored items. The control unit 18 comprises a slide control mechanism 19 with locking hardware, such as solenoids, latches, etc., controlled by a processor 20. The control unit 18 also includes a storage medium 40 in communication with processor 20. In some embodiments, the processor 20 is in communication with a user interface such as a terminal 22. The terminal 22 comprises a keyboard 24 or other input device and a display screen or display 26. In some embodiments, display 26 is a touch screen, which allows a health care professional or user to interact with images displayed on the screen 26 to input data and commands for use by the processor 20 to control the operation of the cabinet 12, instead of using the keyboard 24.

Persons of ordinary skill in the art will appreciate that a mouse or other pointing device (not shown) may be used in combination with display 26 to interact with images displayed on the screen. A device such as a scanner (not shown) for reading machine-readable identification tags on storage spaces and/or on items to be stored may be in electronic communication with the control unit 18 so as to provide the control unit 18 with information regarding the items to be stored in the drawers 16. It should be understood that the present invention is directed to medical devices 10 capable of wireless connection and not necessarily to items that are stored within the medical device 10, unless such items are medical devices with their own wireless capability.

Figure 3:
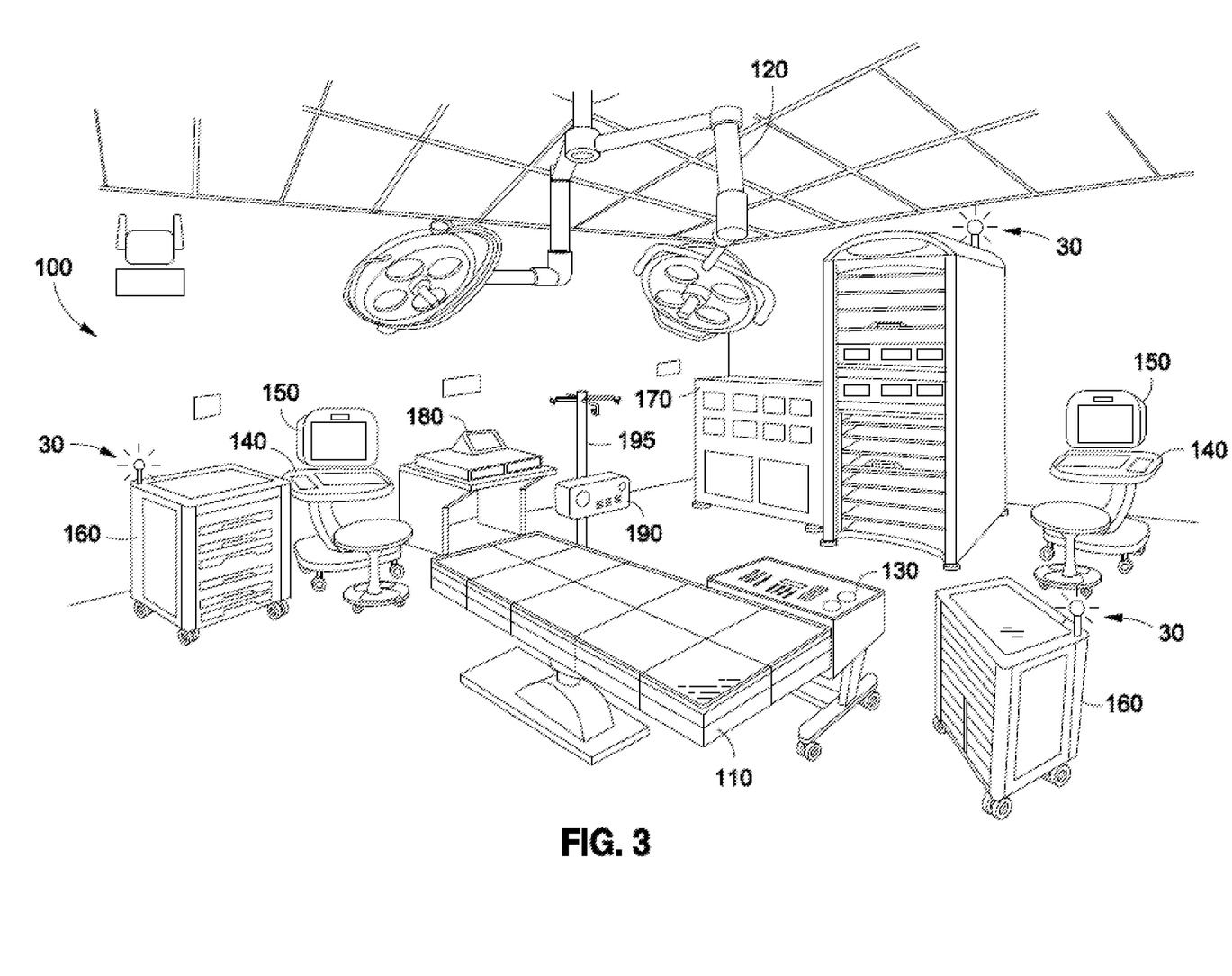
FIG. 3 is a perspective depiction of an exemplary medical treatment area, such as an operating room, in which the disclosed embodiments may be employed.

Referring now to FIG. 3, a perspective depiction of an exemplary operating room 100, in which a medical device 10 may be employed is shown. It is noted that the disclosed embodiments are not limited to an operating room 100, and may be utilized in accordance with any medical treatment area within a medical facility, including, for example, a patient room.

In the exemplary embodiment depicted in FIG. 3, an operating room 100 includes a patient bed 110, a lighting assembly 120, a utensil platform 130, a plurality of terminals 140, a plurality of displays 150, a plurality of inventory storage devices 160, a waste disposal device 170, an electronic monitoring device 180, an intravenous (IV) fluid stand 195 and an infusion pump 190. Operating room 100 may additionally include other equipment as desired, including, for example, anesthesia equipment, defibrillators, vital signs monitors, respiratory ventilators, dialysis machines, etc.

As stated above, "medical device" 10 refers to any device capable of wireless communication, such as dispensing station 15 or inventory storage device 160. It may also refer to individual items, such as pumps, defibrillators, etc. The term may also refer to supplies, such as boxes of surgical instruments, prosthetic devices, etc. These medical devices 10 may be transported and used for a number of patients in a number of medical treatment areas and contain items such as medications used during anesthesia and surgical instruments. Because many nurses and other health care professionals handle the medical devices 10, it may be difficult to ascertain the location or track the movement of the medical devices 10 within the medical facility.

Consequently, equipping certain ones of the medical devices 10 with the ability to expedite their deployment within an operating room 100 is desirable. In accordance with certain exemplary embodiments, medical devices 10, such as dispensing station 15 or inventory storage device 160, include wireless communication device 30. Without being bound by any particular theory, it is believed that equipping the medical devices 10 with wireless communication device 30 will reduce the time necessary to integrate the medical devices 10 into an operating room 100 or other medical treatment area and assign the medical devices 10 to a patient.

Figure 4:
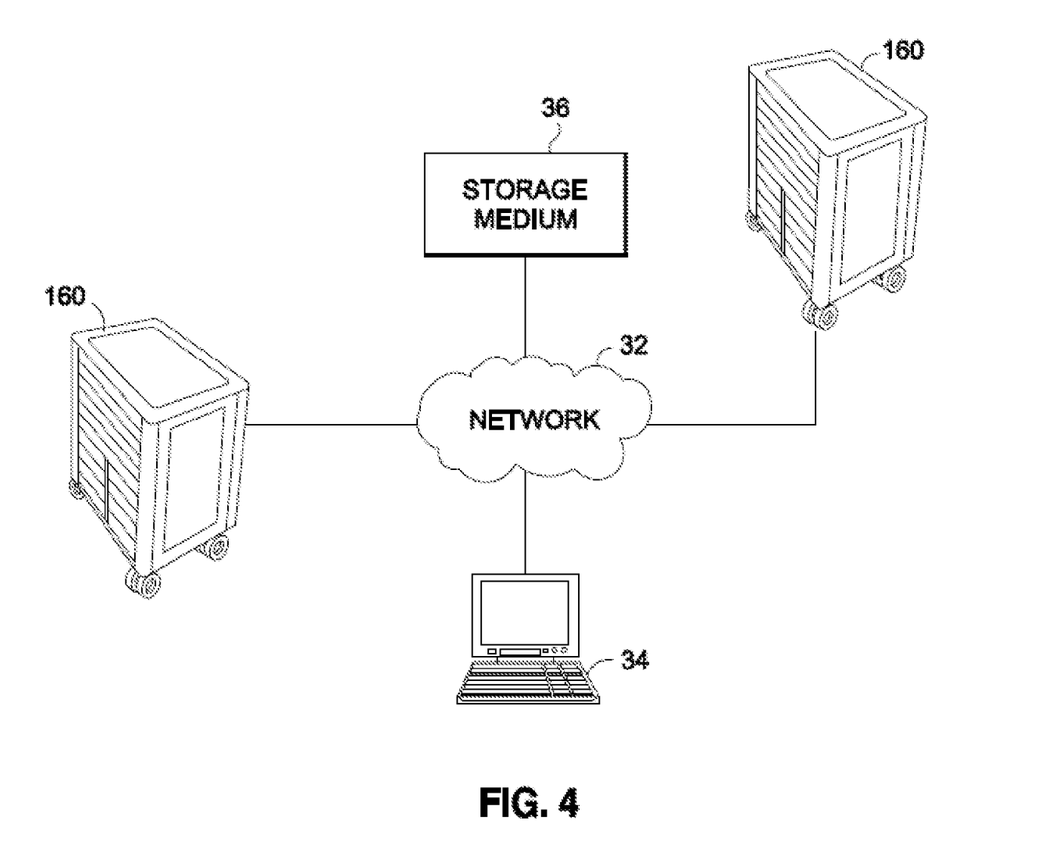
FIG. 4 is a schematic illustration of medical devices in communication with a medical facility network, according to disclosed embodiments.

Referring now to FIG. 2 and FIG. 4, in certain embodiments the dispensing station 15 is part of a system 31 and is linked via a medical facility network 32 to a central computer 34 with access to a centralized storage device such as storage medium 36. As shown in FIG. 4, in an exemplary embodiment, medical facility network 32 is in communication with a storage medium 36 and a plurality of inventory storage devices 160. The devices in communication with medical facility network 32 may also be referred to as entities or nodes. The arrangement of the network 32 and the nodes may take many different forms, and the depicted arrangements in FIGS. 2 and 4 are exemplary only.

In certain embodiments, medical facility network 32 is configured to be able to physically connect to the medical devices 10 and wirelessly connect to the medical devices 10. Technologies suitable for wireless communication include Bluetooth, Zigbee, radio frequency identification (RFID) and ultra-wide band (UWB), to name a few.

Connection of medical facility network 32 to the medical devices 10 allows the medical devices 10 to share and exchange data with other medical devices 10 and entities such as central computer 34 and storage medium 36. Storage medium 36 may include, for example, one or more databases having patient-specific information and information regarding items currently stored or are to be stored in the dispensing station 15 or inventory storage device 160. In these embodiments, the medical facility network 32 provides the means for the control unit 18 to automatically obtain patient-specific information and information regarding stored items. In certain exemplary embodiment, medical facility network 32 is connected to the Internet (not shown).

Because medical facilities employ a very large number of different medical devices 10, it is desirable to limit the wireless range of the medical devices 10, so as to limit interference between the medical devices 10 and other equipment. In a preferred embodiment, the wireless range of the medical devices 10 is limited to approximately the medical treatment area. Such a limit on the wireless range may be achieved by limiting the power level of the medical device 10 to a maximum threshold value.

Alternatively, rather than limiting the wireless range of the medical devices 10, employing physical or electromagnetic barriers that prevent the transmitting and receiving of wireless communication signals outside of the desired area may be used. For example, in a typical operating room 100, the walls may be lined with lead, thereby preventing transmission of wireless communication signals into and out of the room.

In should be appreciated that the medical devices 10 may be secure or unsecure in their connection to medical facility network 32. However, it is desirable for the medical devices and the medical facility network to be in compliance with the Health Insurance Portability & Accountability Act of 1996 (HIPAA) and other relevant standards.

In certain aspects, medical facility network 32 comprises a facility-wide network. In certain other aspects, medical facility network 32 comprises a local network. A local network may include, for example, a network that is dedicated to a single room.

Figure 5:
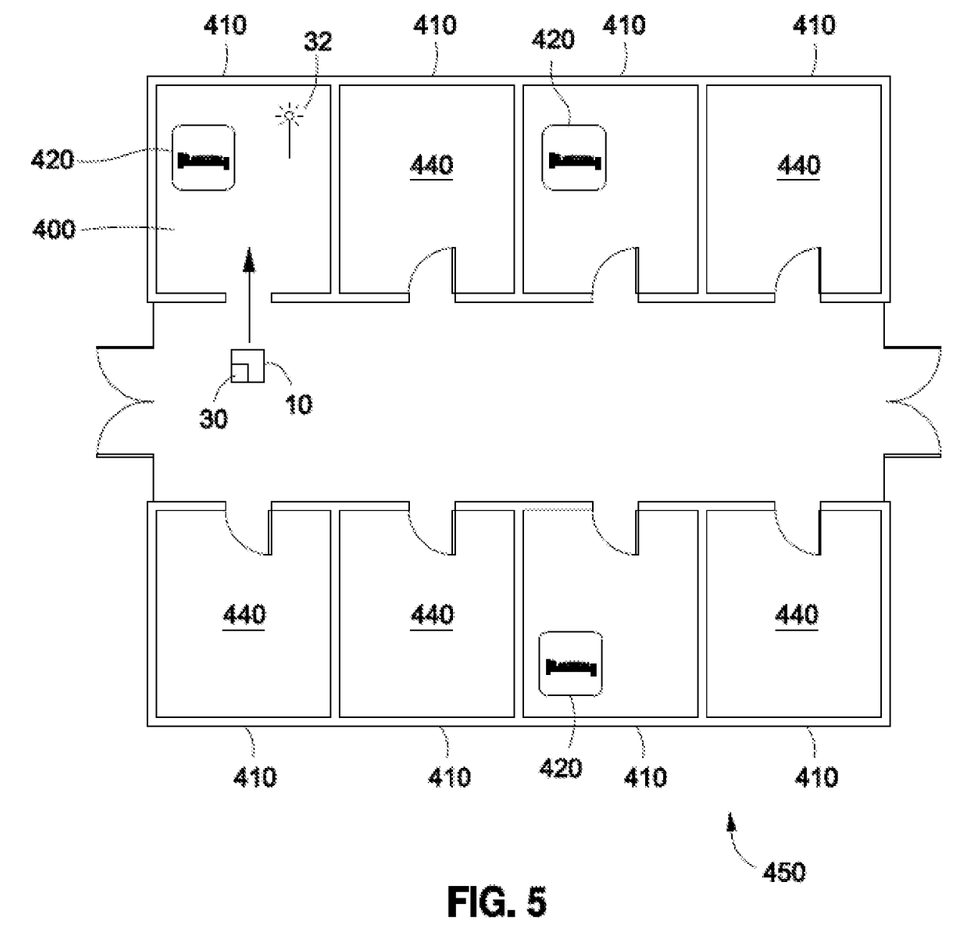
FIG. 5 is a schematic depiction of a medical device entering a medical treatment area, according to disclosed embodiments.

Referring now to FIG. 5, a schematically illustrated example of a medical device 10 entering a medical treatment area 400 is shown. In certain embodiments, medical treatment area 400 comprises a patient room 410 in a medical facility 450. The medical treatment area 400 could also be an operating room, an examination room, etc., as explained earlier.

As shown in FIG. 5, a plurality of patient rooms 410 may be part of medical facility 450. Patient rooms 410 may be occupied by patients 420 or may be vacant 440. In certain embodiments, medical device 10 and medical treatment area 400 both have wireless communication devices 30 allowing wireless interaction. In certain embodiments, the wireless communication device 30 of medical treatment area 400 is connected to medical facility network 32.

As medical device 10 enters treatment area 400, medical device 10 and medical facility network 32 interact through wireless communication devices 30 to exchange data such as patient records and medical device 10 information. In certain embodiments, medical facility network 32 assigns medical device 10 to the specific patient 420 within medical treatment area 400. The exchange of this information will be further described in detail with reference to FIGS. 6-8.

Figure 6:
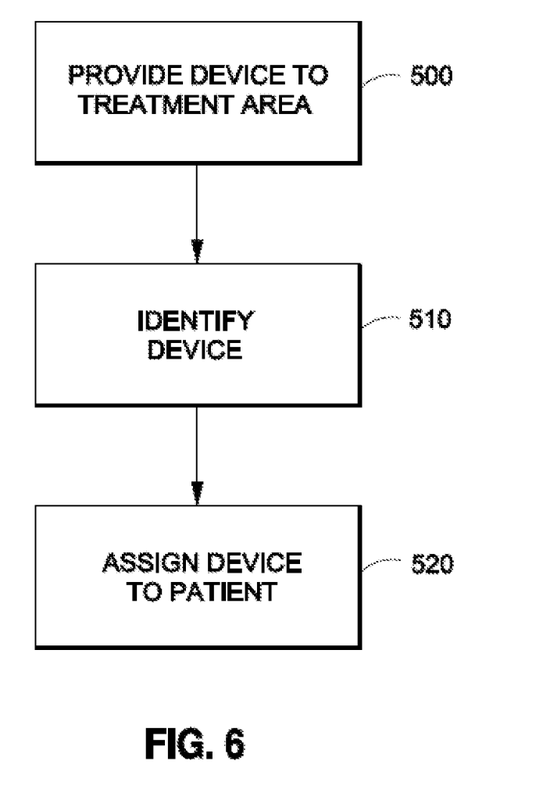
FIG. 6 is a flow diagram illustrating a method of controlling inventory in a medical facility, according to disclosed embodiments.

Referring now to FIG. 6, a flow diagram illustrating a method of controlling inventory in a medical facility, according to certain disclosed embodiments is shown. Initially, a medical device 10 is provided into a medical treatment area 400 at step 500. Medical device 10 may be provided in any manner, such as by manually rolling medical device 10 into medical treatment area 400 if medical device 10 includes wheels, such as dispensing station 15. In other embodiments, medical device 10 may be carried into medical treatment area 400. Such is typically the case for "renegade" medical devices that a sales representative may bring in to the medical treatment area 400. Also, smaller medical devices 10, such as pumps, etc., can be carried into the medical treatment area 400.

Upon introduction of medical device 10 into medical treatment area 400, medical facility network 32 automatically detects and identifies the medical device 10 at step 510. Such detection and identification is achieved by either the medical device 10 initiating transmission of a signal to inform medical facility network 32 that the medical device 10 is within wireless range or by medical facility network 32 periodically transmitting signals to determine which medical devices 10 are within wireless range. In response, the medical device 10 replies to the medical facility network 32 with a message.

Figure 7:
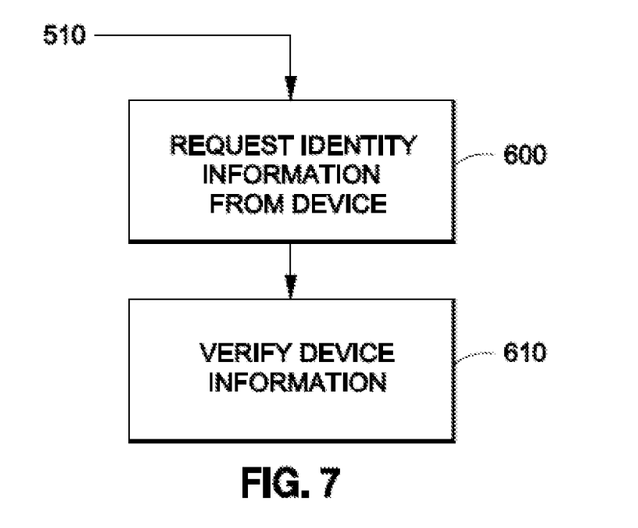
FIG. 7 is a flow diagram illustrating a method of identifying a medical device by a medical facility network, according to disclosed embodiments.

Referring briefly to FIG. 7, identification step 510 is further defined. At step 600, after communication is established the medical facility network 32 requests identity information from medical device 10. Such request may be accomplished by medical facility network 32 transmitting a request signal to the medical device 10.

In response to the information request, medical device 10 transmits a signal to medical facility network 32 comprising the requested device identity information. In certain embodiments, the identity information comprises an electronic serial number associated with the medical device 10. In certain embodiments, other device identifiers may be used.

Once medical facility network 32 receives medical device 10 identity information, a verification process may be performed to verify the identity of the medical device 10, in step 610. Verification of the identity information may be achieved, for example, by the medical facility network 32 inquiring as to whether a medical device record exists for the medical device 10. For example, medical devices 10 already inventoried by the medical facility 450 have a medical device record associated with them.

For medical devices 10 not already inventoried by medical facility 450 such as "renegade" devices, a medical device record does not exist. For these non-inventoried medical devices 10, medical facility network 32 may create a medical device record by retrieving medical device information such as product information from the Internet or local storage. These new medical device records may then be saved in remote storage medium 36 or in medical device 10 itself, such as in storage medium 40 of dispensing station 15.

An additional verification may be performed by a health care professional or user operating the medical devices 10 and comparing the medical devices 10 to the medical device records relating to the patient. This step may be routinely performed as an additional or final check to ensure that the medical device 10 is correct for that particular patient.

For example, for medical devices 10 containing surgical equipment, if a particular instrument or set of instruments was needed but not present as part of medical device 10, the health care professional or user could reject the medical device 10 and perform a search for the correct medical device 10. During times such as emergency surgeries, it is imperative that the correct medical device 10 be found quickly and assigned to the patient. Additionally, for medical devices 10 containing medications, it is imperative that a medical device 10 containing a medication with the correct dosage be utilized. For example, a medical device 10 containing medications for a children's wing in the hospital may contain similar medications with much lower concentrations than a medical device 10 in the main part of the hospital. An error in assigning a child an adult concentration or dosage could prove fatal. Thus, this additional verification step is desirable considering the adverse consequences failing to perform it can have.

Referring back to FIG. 6, after medical device 10 is identified in step 510, the medical device 10 is assigned to a patient in step 520. The assignment of medical device 10 to a patient is an important step in controlling inventory and providing proper and complete billing. Once medical device 10 has been assigned to a patient, that patient may be billed for the use of medical device 10, or for those medications, etc., removed from the medical device 10. Furthermore, assignment of medical device 10 to a patient allows medical facility personnel and planners to determine which medical devices 10 are more frequently used for certain surgical procedures and to better plan accordingly. Additionally, if a medical device 10 or an item contained within medical device 10 is recalled for safety reasons, the patient that had been associated with that medical device 10 may be easily notified of the recall. Lastly, assignment of medical devices 10 to patients allows medical facility personnel to determine how many "renegade" medical devices are used within its medical facility.

Figure 8:
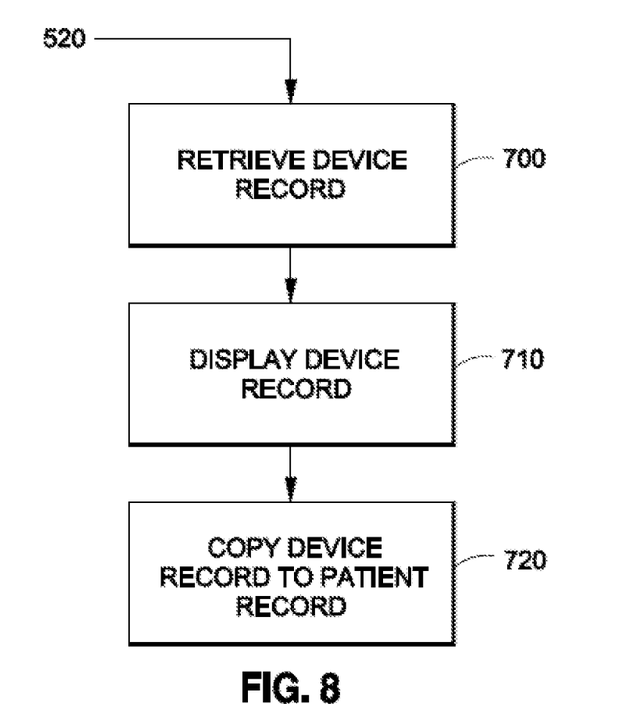
FIG. 8 is a flow diagram illustrating a method of assigning a medical device to a patient, according to disclosed embodiments.

Referring now to FIG. 8, a flow diagram illustrating a method of assigning a medical device 10 to a patient according to certain disclosed embodiments is shown. At step 700, medical facility network 32 retrieves the medical device record from the storage medium 40 of the medical device 10. The medical device record is then displayed for a health care professional or user to view at step 710. The medical device record may be displayed on display 26 of dispensing station 15 or on a display separate from the medical device 10 such as display 150.

As described above in the discussion of FIG. 6, a health care professional or user may perform verification of medical device 10 by inspecting the medical device 10 and comparing the medical device 10 to its medical device record. The displaying of the medical device record allows a health care professional or user to ascertain that the correct medical device 10 will be assigned to the patient.

After the health care professional or user is satisfied that the correct medical device 10 is present, in some embodiments, the medical device record associated with medical device 10 is copied into the patient record in central storage medium 36 at step 720. Copying the medical device record into the patient record provides pertinent information about the medical device 10 such as product information, i.e., make, model, batch, etc. so that if that information is needed later, it is readily available. In some embodiments, rather than the entire medical device record, a portion of the medical device record is copied into the patient record. Still, in other embodiments, the electronic serial number associated with the medical device 10 or other identifiers are copied into the patient record. These last two options provide some information about medical device 10, but require that a person needing more complete information do a product search via the internet or by contacting the manufacturer of medical device 10.

When the caregiver is finished using medical device 10, such as is the case when a patient's surgery is complete and the medical device 10 contains surgical equipment, medical device 10 may be discharged from the patient. The discharge may be accomplished by reassigning the medical device 10 from the patient so that further use of the medical device 10 will not be charged to the patient 420. The use of the medical device 10 will remain in the patient record to be used for billing and other purposes. In some embodiments, after the medical device 10 has been assigned to the patient, a billing record is updated to reflect that the patient 420 has used the medical device 10.

In certain embodiments, the medical device discharge is accomplished by noting in the patient record that medical device 10 is no longer assigned to the patient. The change in status may be signified by changing the color of the font of a display medical device record in the patient record from a first color to a second color, e.g., red font to black font, or black font to gray font. Alternatively, the medical device record may have an asterisk associated with it when it is assigned to a patient, and the asterisk may be removed when the medical device is discharged from the patient. Those skilled in the art will recognize that there are a number of ways to reflect that the medical device 10 has been discharged from a patient. As such, these methods of reflecting discharge of the device from the patient are within the scope of the present invention.

While methods of discharging the medical device 10 from patient have been described thus far, the timing of such discharge has not been discussed. As should be appreciated, because medical device 10 and medical treatment area 400 are configured to communicate wirelessly, once these components are no longer within wireless range of each other, medical device 10 is automatically discharged from the patient. For example, once medical device 10 is removed from medical treatment area 400, such as by wheeling medical device 10 out of patient room 410 and into a hallway of the medical facility 450, the patient record is updated to reflect that medical device 10 has been discharged from the patient. Alternatively, should the wireless connectivity with medical treatment area 400 cease to exist the medical device 10 may similarly be discharged from the patient.

Embodiments disclosed herein provide a method and system for controlling inventory of medical devices in a medical facility. As a result of controlling medical devices, patients are provided with the correct medical devices and are accurately billed for the medical devices that they use.

Methods and apparatus of the present invention are intended to be used in conjunction with supply systems such as dispensing station 15, and for medical devices 10 that are used directly with patients, such as pumps, monitors, instruments, etc. The methods and apparatus of the present invention provide an additional safeguard for controlling inventory of medical devices. Additionally, methods and apparatus of the present invention provide a way to detect and track "renegade" medical devices introduced by sales representatives and used in medical procedures at an unknown rate, as long as such devices include wireless communication capability 30.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method of assigning a medical device to a patient, comprising:
    detecting, by one or more computing devices, that a medical device moved into a predefined medical treatment area currently associated with a patient of a medical facility responsive to a wireless connection being formed between a first wireless communication device of the medical device and a second wireless communication device inside the predefined medical treatment area, wherein the wireless connection is formed only when the first and second wireless devices are within a predetermined wireless range defined by the predefined medical treatment area;
    automatically, in response to detecting that the medical device moved into to the medical treatment area, by the one or more computing devices, obtaining identity information identifying the medical device from the medical device over the wireless connection, retrieving, using the obtained identify information, a medical device record associated with the medical device from a storage medium, the storage medium being accessible through the medical facility, and updating a patient record of the patient currently associated with the treatment area to reflect that the medical device has been assigned to the patient currently associated with the treatment area;
    detecting, by the one or more computing devices, that the medical device was removed from the treatment area based on the first wireless communication device of the medical device no longer being detected within the predetermined wireless range of the second wireless communication device; and
    updating, responsive to the first wireless communication device no longer being detected within the predetermined wireless range of the second wireless communication device, the patient record to reflect that the medical device has been discharged from the patient.

2. The method of claim 1, wherein the medical device record comprises the medical device information.

3. The method of claim 1, further comprising:
    displaying the medical device record for a user to view.

4. The method of claim 1, wherein upon assigning the medical device to the patient, a billing record is updated to reflect that the patient has used the medical device.

5. The method of claim 1, wherein the medical treatment area comprises a patient room or surgical room employing physical or electromagnetic barriers that prevent a transmitting or receiving of wireless communication signals outside of the medical treatment area.

6. The method of claim 1, further comprising:
    retrieving, by the one or more computing devices, medical device information from a public network responsive to the medical device being a non-inventoried medical device; and
    creating, by the one or more computing devices, the medical device record for the non-inventoried medical device with the medical device information, in the storage medium.

7. The method of claim 1, further comprising:
    automatically obtaining, in response to detecting that the medical device moved into to the medical treatment area currently associated with the patient, by the one or more computing devices, exchanging with the medical device, over the wireless connection, one or more patient records and medical device information identifying the medical device, the one or more patient records including a patient record of the patient currently associated with the treatment area.

8. A system, comprising:
    a medical facility network having an access to a storage medium; and
    a wireless communication device having a predetermined a wireless range for a predefined treatment area of a medical facility network, the treatment area currently associated with a patient, wherein
    one or more computing devices associated with the medical facility network, the one or more computing devices, in conjunction with the wireless communication device, being configured to:
        automatically identify a medical device in the treatment area currently associated with the patient by obtaining identity information from the medical device responsive to and over a wireless connection being formed inside the predefined treatment area between the wireless communication device and the medical device, wherein the wireless connection is formed only when the medical device is within a predetermined wireless range defined by the predefined treatment area;

upon the wireless connection being formed inside the predefined treatment area between the wireless communication device and the medical device:
  automatically retrieve, responsive to obtaining the identify information, a medical device record from the storage medium, the medical device record associated with the medical device, and
  update a patient record of the patient currently associated with the treatment area with information from the retrieved medical device record to reflect that the medical device has been assigned to the patient currently associated with the predefined treatment area; and
  upon determining that the first wireless communication device is no longer detected within the predetermined wireless range of the second wireless communication device, updating the patient record to reflect that the medical device has been discharged from the patient.

9. The system of claim 8, wherein the medical device record comprises the medical device information.

10. The system of claim 8, wherein the medical treatment area comprises a patient room or surgical room employing physical or electromagnetic barriers that prevent a transmitting or receiving of wireless communication signals outside of the medical treatment area.

11. The system of claim 8, wherein the medical facility network comprises a local network or facility-wide network.

12. The system of claim 8, further comprising:
  a terminal interfacing with the medical facility network; and
  a display in communication with the terminal,
  wherein the medical facility network is user accessible through the terminal.

13. The system of claim 12, wherein upon assigning the medical device to a patient, a billing record is updated to reflect that the patient has used the medical device.

14. The system of claim 8, wherein the one or more computing devices are further configured to retrieve medical device information associated with the medical device from a public network responsive to introduction of the medical device into the medical treatment area and the medical device being a non-inventoried medical device, and to create the medical device record for the non-inventoried medical device with the medical device information, in the storage medium.

15. The system of claim 8, wherein the one or more computing devices are further configured to:
  automatically obtaining, in response to detecting that the medical device moved into to the medical treatment area currently associated with the patient, exchange with the medical device, over the wireless connection, one or more patient records and medical device information identifying the medical device, the one or more patient records including a patient record of the patient currently associated with the treatment area.

16. A non-transitory computer-readable medium comprising instructions stored thereon that, when executed by one or more computing devices, cause the one or more computing devices to perform a method of assigning a medical device to a patient, comprising:
  detecting, by one or more computing devices, that a medical device moved into a predefined medical treatment area currently associated with a patient of a medical facility responsive to a wireless connection being formed inside the treatment area between a first wireless communication device of the medical device and a second wireless communication device inside the treatment area, wherein the wireless connection is formed only when the first and second wireless devices are within a predetermined wireless range defined by the predefined medical treatment area;
  automatically obtaining, from the medical device, in response to detecting that the medical device moved into to the medical treatment area, by the one or more computing devices, identity information identifying the medical device;
  automatically, using the obtained identify information, by the one or more computing devices, retrieving a medical device record associated with the medical device from the medical facility from a storage medium that is accessible through a network of the medical facility;
  automatically, by the one or more computing devices responsive to detecting the medical device moved into the treatment area and obtaining the identity information, updating a patient record of the patient currently associated with the treatment area to reflect that the medical device has been assigned to a patient currently within the treatment area;
  determining that the first wireless communication device is no longer detected within the predetermined wireless range of the second wireless communication device;
  upon determining that the first wireless communication device is no longer detected within the predetermined wireless range of the second wireless communication device, updating the patient record to reflect that the medical device has been discharged from the patient; and
  displaying, on a display device, the medical device record.

17. The non-transitory computer readable medium of claim 16, the method further comprising:
  automatically obtaining, in response to detecting that the medical device moved into to the medical treatment area currently associated with the patient, by the one or more computing devices, exchanging with the medical device, over the wireless connection, one or more patient records and medical device information identifying the medical device, the one or more patient records including a patient record of the patient currently associated with the treatment area.

* * * * *